United States Patent [19]

Karpov et al.

[11] Patent Number: 4,569,576

[45] Date of Patent: Feb. 11, 1986

[54] METHOD AND DEVICE FOR DETERMINING CORNEA SURFACE TOPOGRAPHY

[75] Inventors: Alexandr V. Karpov, Moskovskaya; Anatoly A. Kivaev; Solomon A. Elkind, both of Moscow; Garri N. Orlov, Moskovskaya; Nikolai I. Lukin, Moskovskaya; Mikhail S. Gashnev, Moskovskaya; Gennady A. Ososkov, Moskovskaya; Valentin I. Prikhodko, Moskovskaya; Vladimir F. Zavyalov, Moskovskaya, all of U.S.S.R.

[73] Assignee: Moskovsky Nauchno-Issledovatelsky Institut Glaznykh Boleznei Imeni Gelmgoltsa, Moscow, U.S.S.R.

[21] Appl. No.: 413,395

[22] Filed: Aug. 31, 1982

[51] Int. Cl.$^4$ ............................................. A61B 3/10
[52] U.S. Cl. .................................... 351/212; 351/247
[58] Field of Search ..................... 351/206, 212, 247

[56] References Cited

U.S. PATENT DOCUMENTS

| 2,016,780 | 10/1935 | Hartinger | 88/20 |
|---|---|---|---|
| 3,248,162 | 4/1966 | Knoll | 351/212 |
| 3,598,478 | 8/1971 | Townsley | |
| 3,781,096 | 12/1973 | Townsley | |
| 3,797,921 | 3/1974 | Kilmer et al. | 351/7 |
| 4,159,867 | 7/1979 | Achetz et al. | |

FOREIGN PATENT DOCUMENTS

| 913872 | 12/1962 | United Kingdom . |
|---|---|---|
| 1145721 | 3/1969 | United Kingdom . |
| 1286887 | 8/1972 | United Kingdom . |

OTHER PUBLICATIONS

Hage, Inspec, A New Photokeratoscopic Technique, Aug. 1976.

N. M. Nikitiuk—Microprocessors and Microcomputers, Employment in Instrument Engineering and Scientific Research, Moscow Energiozdat,—1981.

F. Vaida, A. Chakagny—Microcomputers—Moscow, Engeria Publ.,—1980.

Le Contact Bulletin d'Informations Traitant de l'Optique de Contact Nov. 25, 1967—Coaxial Radii Measuring and Definition.

*Primary Examiner*—Rodney B. Bovernick
*Attorney, Agent, or Firm*—Fleit, Jacobson, Cohn & Price

[57] ABSTRACT

A device for determining the topography of the cornea surface, realizing a method for determining the cornea surface topography, comprises a frame carrying a light source, an objective lens, a light detector, and an array of measuring marks. Said array of measuring marks is a combination of two mark groups, one group being a plurality of ring-shaped marks arranged one after another, axially along the frame and perpendicular to the lens optical axis, while the other group is a plurality of lines arranged lengthwise along the frame to intersect every ring mark and produce, in the light detector, an image consisting of concentric annular patterns and intersecting lines of the radial grid. After a flat image of the array image is obtained, coordinates of image points are measured for specific topographic angles, and corrections are introduced in accordance with the curvature of the radial grid lines.

11 Claims, 11 Drawing Figures

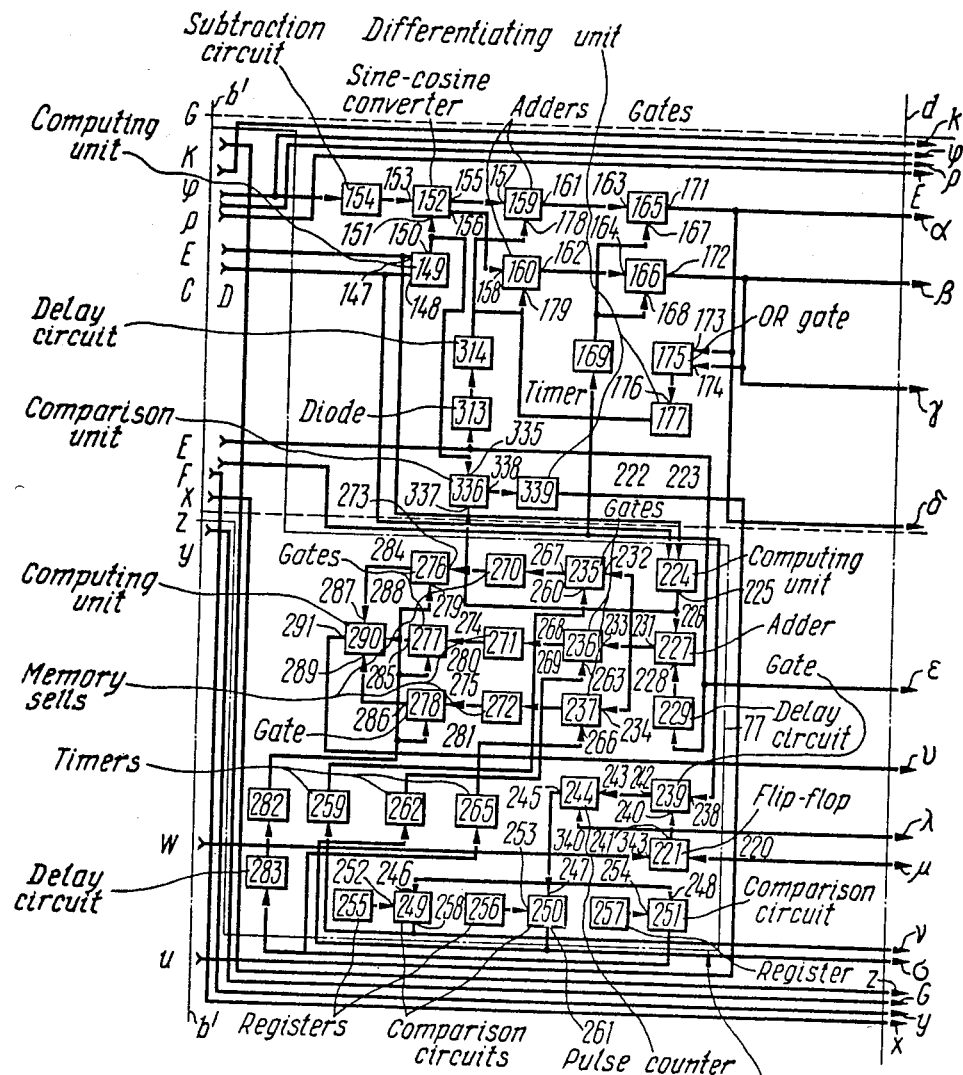
FIG. 5a"
Generator of electrical signals representing the mean linewidth of the central ring image of the array of measuring marks

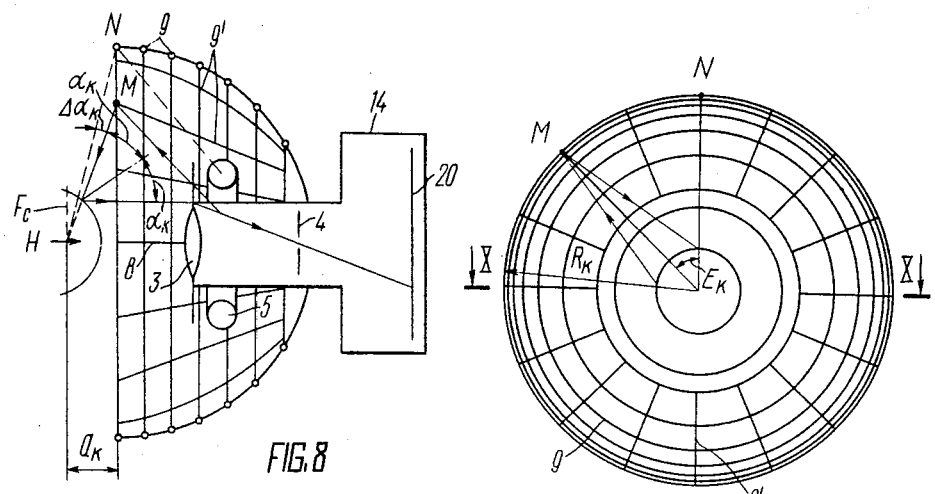
FIG.8
FIG.9
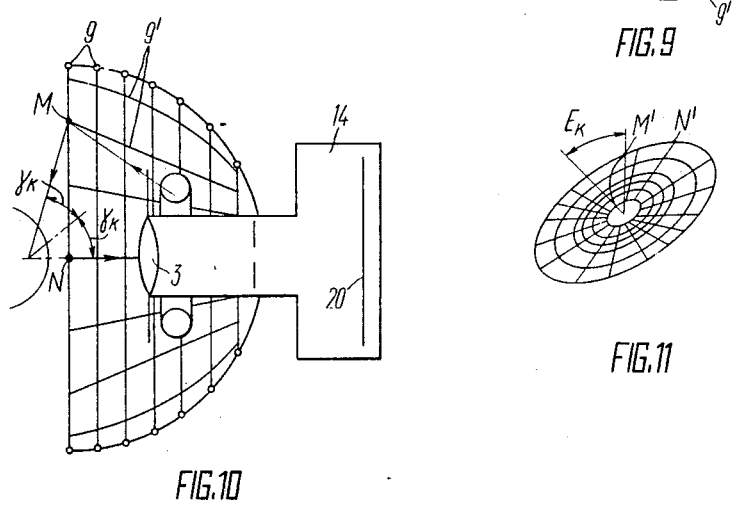
FIG.10
FIG.11

METHOD AND DEVICE FOR DETERMINING CORNEA SURFACE TOPOGRAPHY

FIELD OF THE INVENTION

The present invention relates to medical engineering and to eye examining instruments. More specifically, this invention pertains to a method and device for determining the surface topography of the cornea of the human eye.

The invention can be used to advantage for contact lens vision correction by determining geometrical parameters of the cornea surface in order to provide a perfect fit of the contact lens inner surface. The invention can also used in eye microsurgery, for example, to determine the cornea surface topography prior to and after the operation with a view to improve surgery techniques. This invention can be used, in addition, to measure and monitor optical surfaces similar to cornea, for example, contact lens surfaces.

BRIEF DESCRIPTION OF THE PRIOR ART

Ophthalmologists use many methods and apparatuses for determining the cornea surface topography, primarily for contact lens vision correction. Such methods and devices should, basically, satisfy three conditions: they should be capable of determining the cornea surface topography in all meridian sections of said surface, be highly precise irrespective of the degree of curvature of the cornea, and they should not take too much time to obtain results.

Known methods and devices are not completely satisfactory in these respects. In consequence, methods and devices capable of combining high precision of determination of coordinates of profile points in all meridian sections of the cornea surface suitable for all types of corneas with promptness of examination could be of great practical value in terms of practical application.

Known in the art is an analytical method for determining the cornea surface topography (cf., for example, Le Contact, No. 29, 1972) whereby a cross-shaped mark image produced by the reflective surface of the investigated cornea is recorded photographically. One picture contains information about two orthogonal cornea surface sections. The mark should be gradually turned in order to obtain information about the whole cornea surface in a series of pictures. The processed film is used to measure the radial coordinates of mark image points to be later incorporated in the analytical calculation of the cornea surface.

The above description demonstrates that the method is laborious, involves making series of shots, but fails to provide accurate enough measurements of the cornea topographic features, particularly of those with complex surfaces.

Also known in the art is a method for determining the cornea surface topography (cf., for example, U.S. Pat. No. 3,781,096, Cl. 351/13, Dec. 25, 1973) whereby an array of target rings are projected onto the cornea in order to obtain a flat image of said array and measure the coordinates of image points for specified topographic angles. Target rings are seven illuminated annular slots. The above mentioned image contains information on the whole of the cornea surface to be examined.

When the above method is used to determine the cornea surface topography, one can never, in practical terms, avoid deviations of topographic angles from specified ones, which are due to appear because of individual peculiarities of a cornea. Such deviations reduce, and very often substantially, the accuracy of topography determination.

A solution of sorts was proposed, embodied in devices for determining the cornea surface topography. These device essentially comprise a frame or a housing movable relative to a support and carrying an objective lens, a light source, an array of measuring marks arranged symmetrically relative to the objective lens optical axis in order to direct the luminous radiation to the cornea surface, and a light detector whose sensing element is positioned in the plane perpendicular to the lens optical axis and downstream said luminous radiation reflected from the cornea surface, after said objective lens.

An apparatus for determining the cornea contour (cf., U.S. Pat. No. 3,598,478 Cl. 351/6, Aug. 10, 1971) comprises a measuring mark array made as annular slots arranged on the conical shell of the housing and illuminated by a light source located inside that housing, the light detector being a photographic camera.

In order to determine the cornea surface topography by means of this apparatus, the image of the measuring marks produced by the reflecting cornea surface is directed by the lens to the photographic film to be developed later on. After development of the film, the suitable measurements are made. The coordinates of the mark image points thus obtained are compared with the coordinates of such points produced by some standard, for example, spherical pattern. The results of the comparison yield coordinates of profile points of the cornea surface meridian section. The angles constituted by beams incident from some point of the measuring mark onto the cornea surface and the standard surface and the lens optical axis are equal for any cornea surfaces, that is are preassigned angles.

The above apparatus has no diaphragm in the rear focal plane of the lens and, consequently, the depth of focus is insufficient to provide a sharp image of all marks on the film. Short distance between the measuring marks and the cornea surface results in that the angles formed by the beams incident onto the cornea surface from the measuring mark points and the lens optical axis are essentially the functions of the cornea surface curvature, particularly the degree of asphericity thereof. The accuracy of determining the cornea surface topography is, therefore, substantially lower for intensely aspheric corneas, for example, in case of keratoconus, as compared to corneas characterized by normal or slightasphericity. Photographic film used as a light detector is one more disadvantage because the results of the determination of the cornea topography cannot be promptly made available.

The above deficiencies are also inherent in the apparatus for determining corneal radius (cf., U.S. Pat. No. 3,797,921, Cl. 351/7, Mar. 19, 1974), which is similar to that described above, wherein measuring marks are also annular slots arranged on a spherically concave screen.

A device for measuring the curvature of the cornea (cf., U.S. Pat. No. 4,159,867, Cl. 351/6, July. 3, 1979) comprises measuring marks whch are individual point light sources arranged on a spherically concave surface, and a light detector made as a converter of the optical image into an electrical signal, which is electrically coupled to a computer furnished with a generator of electrical signals representing the coordinates of the cornea surface points.

In the above device the image is recorded as an electrical signal to be later converted into signals representing the coordinates of the cornea surface points. This appreciably speeds up the process of determination of the cornea surface topography. However, the device is incapable of handling profile shapes in all meridian sections of the cornea surface since, as mentioned above, the measuring mark is composed of individual point light sources. Moreover, the depth of sharp focus is insufficient and measuring marks are too closely located to the surface of the cornea, the same disadvantages as those inherent in the apparatus claimed in the U.S. Pat. No. 3,598,478.

SUMMARY OF THE INVENTION

It is an object of this invention to provide a method for determining the cornea surface topography and a device realizing this method so that corrections could be introduced for topographic angles to make for irregularities of the cornea shape.

Another object of the invention is to provide a device for determining the cornea surface topography, whereby subjective operator's errors in determination of topography could be eliminated.

The invention provides a method for determining the cornea surface topography, comprising the steps of: projecting an array of measuring marks onto the cornea to obtain a flat image of said array, and measuring the coordinates of the image points for specified topographic angles, and according to the invention, projecting a measuring mark array which is a plurality of annular marks producing, when projected onto the cornea, several concentric ring-shaped patterns and a plurality of linear marks intersecting former annular marks and producing, when projected onto the cornea, a radial grid, measuring the curvature of lines of the radial grid, and introducing a correction for topographic angles in accordance with the measured curvature of the radial grid lines.

The invention also provides a device for determining the cornea surface topography, comprising a frame movable relative to a mounting and carrying a light source and an array of measuring marks, wherein, according to the invention, the measuring mark array is a combination of two mark groups, one group being a plurality of known annular marks arranged axially one after another along the frame perpendicular to the lens optical axis, while the other group is a plurality of lines arranged lengthwise along the frame and intersecting each annular mark.

The accuracy of determining the topography of corneas of any shape is substantially stepped up by the existing capability to introduce corrections for specified topographic angles with the use of a measuring mark array made as a combination of two groups of marks.

The annular marks should, preferably, be reflective, while the light source should be provided with a luminous body whose center is positioned on the lens optical axis.

The annular marks should, advisably, have a ring-shaped cross-section.

The annular marks should, profitably, be trapezium shaped in their cross-sections.

The side of the trapezium facing the lens optical axis should, effectively, be a portion of a parabola arranged so that the focal point thereof coincides with the axis of the luminous body of the light source.

Trapezium-shaped cross-section of annular marks permits formation of the image of the light source luminous body at a substantially longer distance, or even infinitely longer distance (when one side of the trapezium is a parabola), relative to the cornea surface without any change in the dimensions of the device. The immediate effect of this arrangement is a significant improvement of the topography determination accuracy, particularly in dealing with intricately-shaped corneas.

A diaphragm should, advisably, be placed in the rear focal plane of the lens.

In addition to improvement of image crispness, the diaphragm also contributes to more accurate determination of corrections to specified topographic angles.

When the light detector is a converter of the optical image into an electrical signal, electrically coupled to a generator of electrical signals representing the coordinates of the cornea surface points, the device should, preferably, also comprise a visual display electrically connected to said converter. In this manner the final information on the cornea surface shape can be very promptly obtained and the the process of aiming the device onto the cornea becomes much easier for an operator.

The device should, usefully, comprise a generator of electrical signals representing the mean linewidth of the central ring image in the measuring mark array and a generator of electrical signals representing the coordinates of the central ring image center of the measuring mark array, whose inputs are electrically connected with outputs of the converter of the optical image into an electrical signal, a drive secured to the frame in order to move said frame relative to the mounting, and a control unit electrically connected to said drive, whose inputs are electrically coupled with the generator of electrical signals representing the mean linewidth of the central ring image in the measuring mark array and with the generator of electrical signals representing the coordinates of the central ring image center of the measuring mark array. Such arrangement permits automation of the process of aiming the device onto the surface of the cornea and improve the accuracy of the cornea surface topography determination by eliminating the subjective operator's errors.

BRIEF DESCRIPTION OF THE DRAWINGS

The invention will now be described in more detail, by way of example, with reference to the accompanying drawings, in which:

FIG. 8 shows a schematic of a projection of beams incident upon the cornea surface and reflected therefrom onto the meridian plane, according to the invention;

FIG. 9 shows a view taken along the arrow H of FIG. 8 of an array of measuring marks and the cornea, and beam projections, according to the invention;

FIG. 10 shows a sectional view taken along line X—X of FIG. 9, according to the invention;

FIG. 11 shows a view of an image of a measuring mark array in the light detector plane, according to the invention.

DETAILED DESCRIPTION OF THE INVENTION

Figure 1:
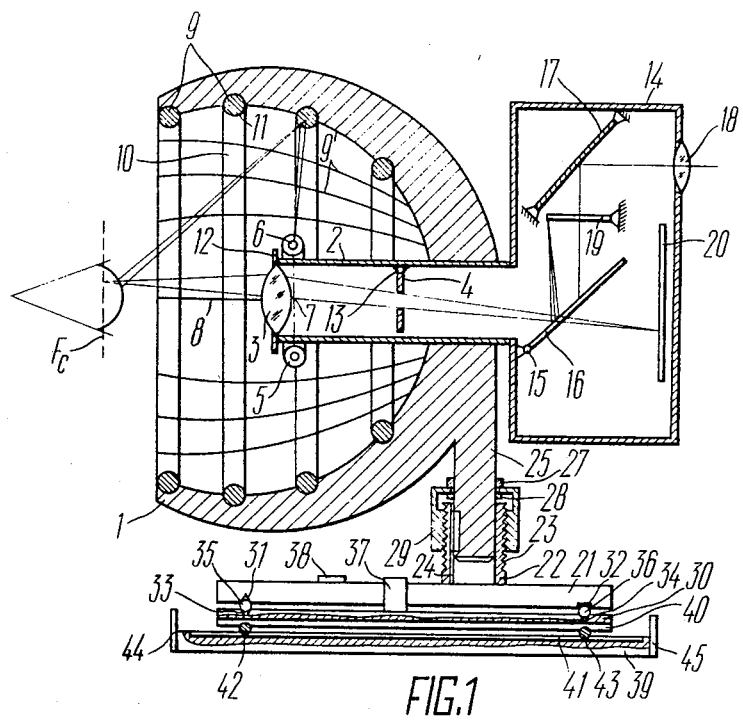
FIG. 1 shows a sectional view along the optical axis of a device for determining the cornea surface topography, featuring a mirror reflective working surface of a measuring mark whose cross-section is circular in shape, according to the invention.

A method for determining the cornea surface topography, comprising the steps of: projecting an array of measuring marks onto the cornea, said array being composed of a plurality of annular marks producing, when projected onto the cornea, several concentric ring-like patterns and a plurality of linear marks intersecting said annular marks and producing, when projected onto the cornea, a radial grid; obtaining a flat image of this array, and measuring the coordinates of the image points for specified topographic angles and curvatures of the lines of the radial grid; introducing a correction for said specified topographic angles in accordance with the measured curvature of the radial grid lines.

A device for determining the cornea surface topography comprises a frame 1 (FIG. 1) wherein an objective lens 3 is secured by means of a barrel 2. A diaphragm 4 is placed in the barrel 2 in the rear focal plane of the objective lens 3. A light source 5 is mounted on the barrel 2, featuring an annular luminous body 6 whose center 7 is positioned on an optical axis 8 of the lens 3. An array of measuring marks is secured in the frame 1, which is a combination of two groups of marks 9 and 9', one group being a plurality of annular marks arranged axially one after another along the frame 1 and perpendicular to the optical axis 8 of the lens 3, while the other group is a plurality of lines arranged lengthwise along the frame 1 and intersecting each annular mark. A working surface 10 of the marks 9, which receives the luminous radiation directly from the light source 5, is mirror reflective in this embodiment of the device.

In this embodiment the measuring marks 9 have a cross-section shaped like a circle 11. A screen 12 is secured to the barrel 2 to prevent direct light from falling onto the cornea. The diaphragm 4 is mounted on a hinge 13 in the barrel 2.

A light detector is mounted on the frame 1, in this embodiment the light detector is a photographic camera 14 secured on the barrel 2. A mirror 16 is placed by means of a hinge 15 in the camera 14 on the optical axis 8 of the lens 3. The mirror 16 reflects the luminous radiation to a second mirror 17 rigidly secured in the camera 14 and to an eye-piece 18, a grid 19 being positioned in the front focal plane thereof. A sensitive element, a photographic film 20, is placed in he camera 14 in a plane optically coupled with the plane of the grid 19 and perpendicular to the optical axis 8 of the lens 3.

The frame 1 is positioned so that it can move vertically with respect to a platform 21 equipped with a vertical guide 22 having a thread 23 and a key slot 24. The frame 1 also has a vertical guide 25 featuring a key 26 fitted in the slot 24 and an annular projection 27. A nut 29 is secured by means of a ring 28 to the guide 22 so that it can be turned. Vertical travel of the nut 29 is limited by said projection 27.

The platform 21 can travel lengthwise along a platform 30 and features guide grooves 31 and 32. The platform 30 has guide grooves 33 and 34 wherein balls 35 and 36 are fitted. The travel of the platform 21 is limited by stops 37 and 38 attached to the platform 30.

The platform 30 is provided with guiding slots 40 so that it can move lengthwise on a mounting 39 provided with guiding slots 41 fitted with balls 42 and 43. The travelpath of the platform 30 is limited by stops 44 and 45 secured on the mounting 39.

Figure 2:
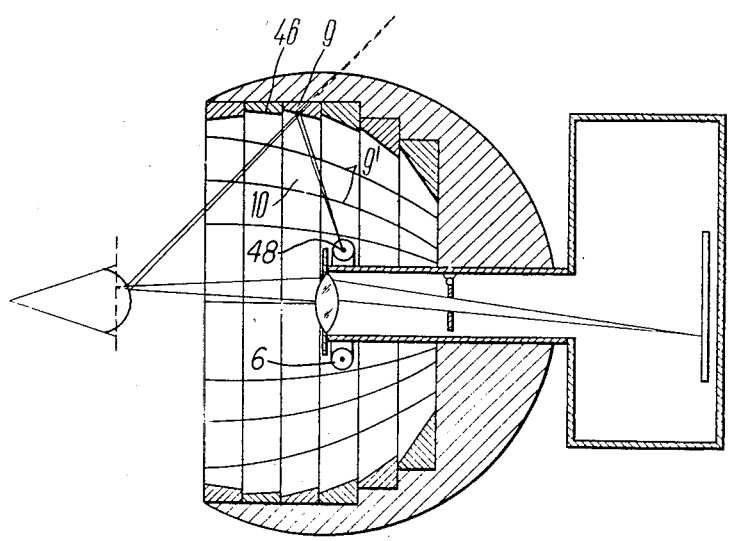
FIG. 2 shows a sectional view taken along the optical axis of a device for determining the cornea surface topography, featuring a mirror reflective working surface of the measuring mark whose cross-section is shaped like a trapezium, according to the invention.

Another embodiment of a device for determining the cornea surface topography differs from the above embodiment in that the measuring marks 9 have a cross-section shaped like a trapezium 46 (FIG. 2).

One more embodiment of a device for determining the cornea surface topography differs from the embodiment of FIG. 1 in that the measuring marks 9 have a cross-section shaped like a trapezium 46 (FIG. 3) whose one side facing the optical axis 8 of the lens 3 is a portion 47 of a parabola. This parabola portion 47 is arranged so that the focal point $F_p$ of the parabola coincides with an axis 48 of the luminous body 6 of the light source 5 and the axes of all parabolas are inclined relative to the optical axis 8 at different angles ranging from 10° to 90°.

Without any detriment to the accuracy and to simplify the manufacturing of the measuring marks 9, the above mentioned side of the trapeziums 46 can be made as a circle segment fairly approximating the parabola portion 47 provided a suitable radius and circle center position are selected to accomodate such approximation.

Figure 3:
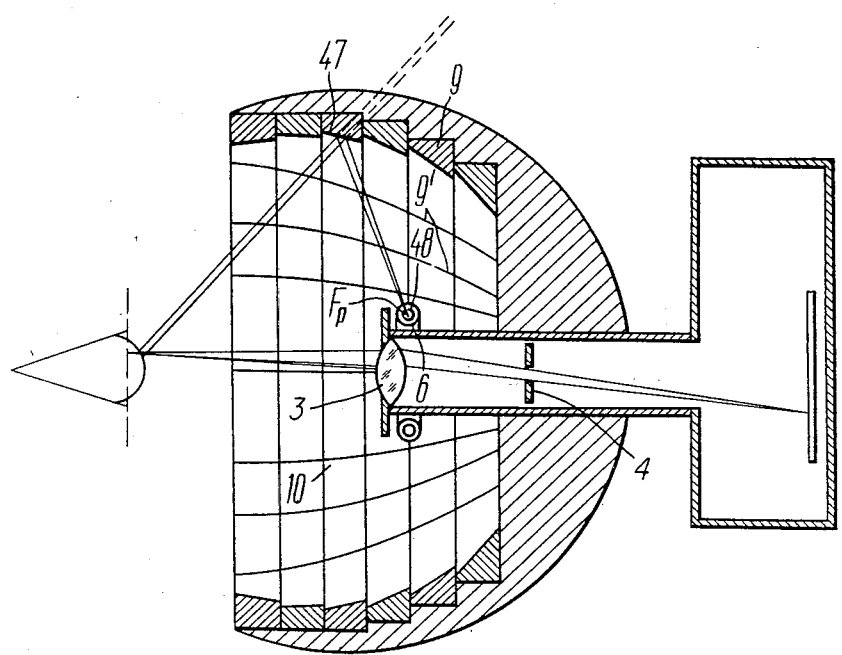
FIG. 3 shows a sectional view taken along the optical axis of a part of a device for determining the cornea surface topography, featuring a mirror reflective working surface of the measuring mark whose cross-section is shaped like, a trapezium, one side thereof being a parabola portion arranged so that the focal point thereof coincides with the axis of a luminous body of a light source, according to the invention.
Figure 4:
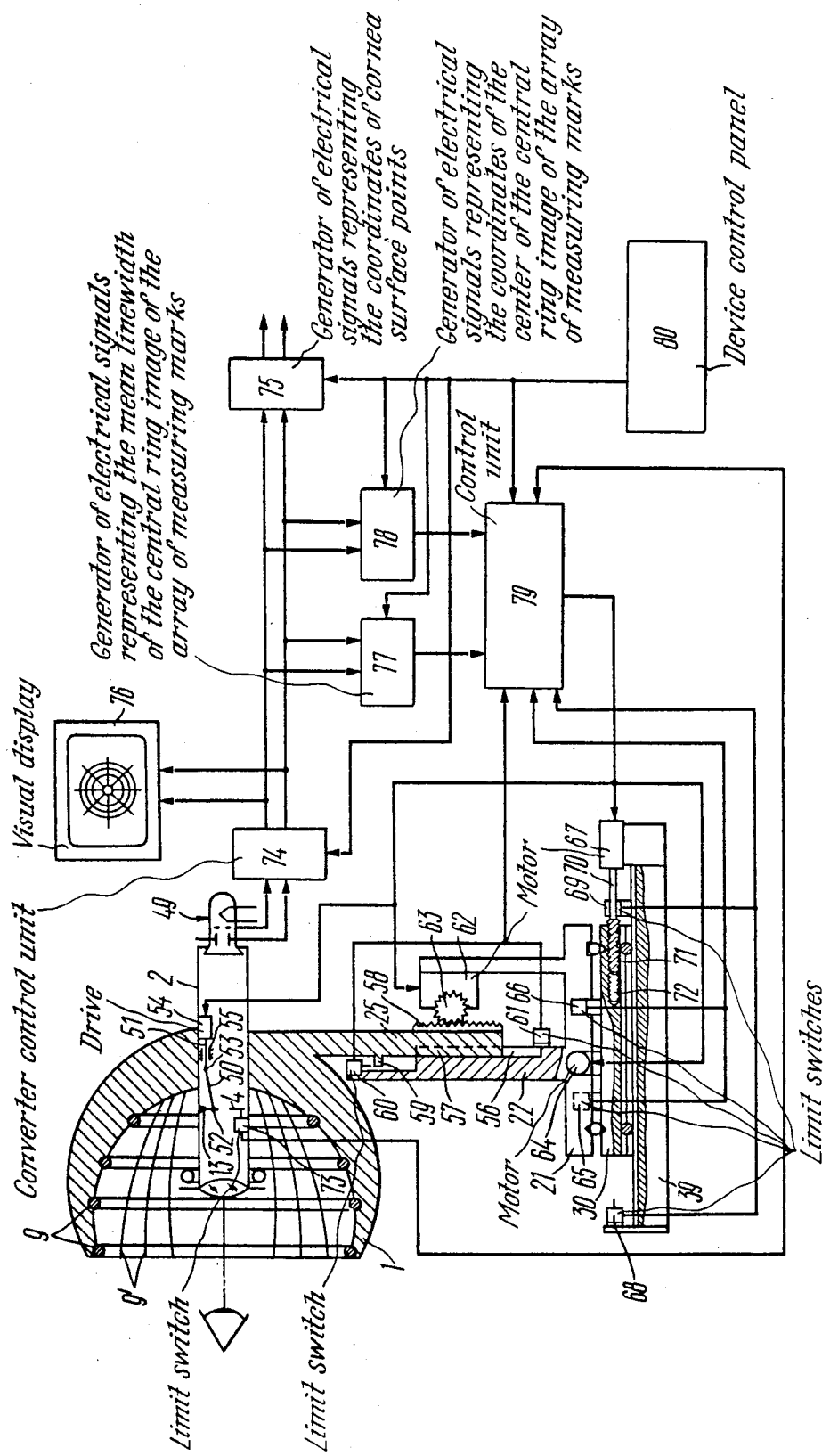
FIG. 4 shows a cut-away view of a device for determining the cornea surface topography, taken along the optical axis of the device, featuring a light detector made as a converter of an optical image into an electrical signal, according to the invention.

The embodiment of a device for determining the cornea surface topography, shown in FIG. 4 differs from the embodiments of FIGS. 1, 2 and 3 in that the light detector here is a converter 49 of an optical image into an electrical signal, which is positioned in the barrel 2. A drive 54, for example, an electromagnet, is connected with the diaphragm 4 installed in the barrel 2 on the hinge 13 by means of links 50 and 51 and hinges 52 and 53. The link 51 is fitted in a guide 55 secured on the barrel 2.

This embodiment of the device comprises a frame 1 which can travel vertically with respect to the platform 21 featuring a vertical guide 22 having a slot 56. The frame 1 is provided with a vertical guide 25 having a projection 57 mated with the slot 56 and a helix rack 58. The guide 25 features a projection 59 limiting the vertical movement of the frame 1. Secured to the platform 21 are limit switches 60 and 61. Also, the device is provided with a drive secured to the frame 1 in order to move it relative to the mounting 39, and a motor 62 with a worm gear-wheel 63, mounted on the platform 21. This platform 21 can move with respect to the platform 30 which in turn can move lengthwise with respect to the mounting 39. The platform 30 carries a motor 64 of said drive and limit switches 65 and 66, while the mounting 39 carries a motor 67 of said drive and limit switches 68 and 69. Motors 64 and 67 are fitted with shafts 70 having thread 71, while the platforms 30 and 21 are provided with identical threaded openings 72 wherein the shafts 70 of the motors 64 and 67 are mated. A limit switch 73 is positioned in the barrel 2.

The converter 49 is electrically connected, via a converter control unit 74, to a generator 75 of electrical signals representing the coordinates of the cornea surface points. Also connected to the converter 49 via the control unit 74 are: a visual display 76, a generator 77 of electrical signals representing the mean linewidth of the central ring image in the measuring mark array, and a generator 78 of electrical signals representing the coordinates of the center of the central ring image in the measuring mark array.

The motors 62, 64 and 67 of the drive of the frame 1 are electrically connected to outputs of a control unit 79 whose inputs are electrically connected to the generators 77 and 78. The control unit 79 is electrically coupled with the drive 54 of the diaphragm 4, and the limit switches 60, 61, 65, 66, 68, 69 and 73. A device control panel 80 is electrically connected to the control units 74 and 79, and to the generators 75, 77 and 78.

In this embodiment of the invention the converter control unit 74 (FIG. 5a) comprises a pulse generator 81 electrically connected to an input 82 of a pulse counter 83. An output 84 of the pulse counter 83 is connected to an input 85 of a sine-cosine converter 86. An output 87 of the counter 83 is connected to an input 88 of a pulse counter 89 whose output 90 is coupled to an input 91 of the converter 86. An output 92 of the converter 86 is connected, via a digital-to-analog converter 93, to an input 94 of the converter 49, that is the vertical-deflecting plates of the cathode-ray tube, while an output 95 of the converter 86 is connected, via a digital-to-analog converter 96, to an input 97 of the converter 49, that is the horizontal-deflecting plates of the cathode-ray tube. An output 98 of the converter 49 is connected, via an analog-to-digital converter 99, to an input 100 of a gate 101 which is a component of the generator 76.

The pulse generator 81 is connected, via a delay circuit 102, to an input 103 of the gate 101 whose output 104 is connected to an input 105 of a comparison circuit 106. An input 107 of the comparison circuit 106 is connected to a register 108, while an output 109 thereof is connected, via a timer 110, to an input 111 of a gate 112. An input 113 of the gate 112 is connected, via a delay circuit 114, to the output 84 of the pulse counter 83. An output 115 of the gate 112 is connected to inputs 116 and 117 of gates 118 and 119, respectively. An input 120 of the gate 119 is connected to an output 121 of a flip-flop 122, which in turn is connected, via an inverter 123, to an input 124 of the gate 118 and, in addition, via the series-connected differentiating unit 125 and a timer 126, to an input 127 of a gate 128. An output 129 of the gate 119 is connected to an input 130 of the gate 128. Outputs 131 and 132 of the gates 118 and 128 are connected, respectively, to memory cells 133 and 134. The memory cell 133 is connected by the output thereof to an input 135 of the flip-flop 122. The outputs of the memory cells 133 and 134 are connected to inputs 136 and 137, respectively, of gates 138 and 139. Inputs 140 and 141 of respective gates 138 and 139, and an input 142 of the flip-flop 122 are connected, via a delay circuit 143, to the output 87 of the pulse counter 83 through a timer 144. Outputs 145 and 146 of respective gates 138 and 139 are connected to inputs 147 and 148 of a computing unit 149 whose output 150 is connected to an input 151 of a sine-cosine converter 152. An input 153 of the sine-cosine converter 152 is connected, via a subtraction circuit 154, to the output 90 of the pulse counter 89. Outputs 155 and 156 of the converter 152 are connected to inputs 157 and 158 of adders 159 and 160, respectively. Outputs 161 and 162 of respective adders 159 and 160 are connected to inputs 163 and 164 of gates 165 and 166 whose inputs 167 and 168 are connected, via a timer 169, to an output 170 of the pulse counter 89. Outputs 171 and 172 of the gates 165 and 166 are connected, respectively, to inputs 173 and 174 of an OR gate 175 whose output 176 is connected, via a differentiating unit 177, to inputs 178 and 179 of the adders 159 and 160.

The outputs 171 and 172 of the gates 165 and 166 are connected, via delay circuits 180 and 181, to inputs 182 and 183 of gates 184 and 185, and to inputs 186 and 187 of comparison circuits 188 and 189 whose inputs 190 and 191 are connected to a register 192. Outputs 193 and 194 of the comparison circuits 188 and 189 are connected, via timers 195 and 196, to inputs 197 and 198 of the gates 185 and 184.

An output 199 of the gate 184 is connected with a control circuit 200 of the control unit 79, which controls the motor 64 and is connected thereto by series-connected gates 201 and 202 of the device control panel 80. An output 203 of the gate 185 is connected to a control circuit 204 of the control unit 79, which controls the operation of the motor 62 and is connected thereto via gates 205 and 206 of the control unit 80.

The outputs 193 and 194 of the comparison circuits 188 and 189 are connected to inputs 207 and 208 of comparison circuits 209 and 210 whose inputs 211 and 212 are connected to a register 213. Outputs 214 and 215 of the comparison circuits 209 and 210 are connected to inputs 216 and 217 of an AND gate 218 whose output 219 is connected to an input 220 of a flip-flop 221 of the generator 77.

In this embodiment of the device some components of the generator 78 prior to the outputs 145 and 146 of the gates 138 and 139 are also used in the generator 77. The outputs 145 and 146 of the gates 138 and 139 are connected to inputs 222 and 223 of a computing unit 224 whose output 225 is connected to an input 226 of an adder 227. An input 228 of the adder 227 is connected, via the series-connected delay circuit 229 and a diode 230, to the output 170 of the pulse counter 89.

An output 231 of the adder 227 is connected to inputs 232, 233 and 234 and gates 235, 236 and 237.

The output 170 of the pulse counter 89 is connected to an input 238 of a gate 239 whose input 240 is connected to an output 241 of the flip-flop 221. An output 242 of the gate 239 is connected to an input 243 of a pulse counter 244 whose output 245 is connected to inputs 246, 247 and 248 of comparison circuits 249, 250 and 251 whose inputs 252, 253 and 254 are connected to registers 255, 256 and 257. An output 258 of the comparison circuit 249 is connected, via a timer 259, to an input 260 of the gate 235. An output 261 of the comparison circuit 250 is connected, via a timer 262, to an input 263 of the gate 236. An output 264 of the comparison circuit 251 is connected, via a timer 265, to an input 266 of the gate 237.

Outputs 267, 268 and 269 of respective gates 235, 236 and 237 are connected to memory cells 270, 271 and 272 which are in turn respectively connected to inputs 273, 274 and 275 of gates 276, 277 and 278. Inputs 279, 280 and 281 of the gates 276, 277 and 278 are connected, via a timer 282 and a delay circuit 283, to the output 264 of the comparison circuit 251.

Outputs 284, 285 and 286 of the gates 276, 277 and 278 are respectively connected to inputs 287, 288 and 289 of a computing unit 290 whose output 291 is connected to an input 292 of an OR gate 293. An output 294 of the OR gate 293 is connected to a control circuit 295 of the control unit 79, which controls the motor 67 and is connected thereto via the series-connected gates 296 and 297 of the control panel 80.

The output 258 of the comparison circuit 249 is connected, via the series-connected delay circuit 298 and a control signal shaping unit 299, to an input 300 of the OR gate 293.

The output 261 of the comparison circuit 250 is connected, via the series-connected delay circuit 301 and a control signal shaping unit 302, to an input 303 of the OR gate 293.

Outputs of the delay circuits 298 and 301 are also connected to inputs 304 and 305 of an OR gate 306 whose output 307 is connected, via the series-connected delay circuit 308, a differentiating unit 309 and the delay circuit 229, to the input 228 of the adder 227. The output of the differentiating unit 309 is also connected to inputs 310 and 311 of the counters 83 and 89.

The output of the differentiating unit 309 is connected, via the series-connected diode 312 and the delay circuit 143, to the input 142 of the flip-flop 122. The output of the diode 312 is also connected to the inputs 140 and 141 of the gates 138 and 139. The output of the differentiating unit 309 is also connected, via the series-connected diode 313 and a delay circuit 314, to the inputs 178 and 179 of the adders 159 and 160.

The output 291 of the computing unit 290 is connected, via a delay circuit 315, to a control circuit 316 of the control unit 79, which is connected in turn to the drive 54 of the diaphragm 4 (FIG. 4). The control circuit 316 (FIG. 5a''') is connected, via diodes 317, 318 and 319, to inputs 320, 321 and 322 of, respectively, flip-flops 323, 324 and 325 whose outputs 326, 327 and 328 are connected to inputs 329, 330 and 331 of the gates 202, 297 and 206 and indication lamps 332, 333 and 334 of the control panel 80.

The output 150 of the computing unit 149 is connected to an input 335 of a comparison circuit 336 whose input 337 is connected to the output 225 of the computing unit 224. An output 338 of the comparison circuit 336 is connected, via a differentiating unit 339, to an input 340 of the pulse counter 244 and, via a diode 341, to the input of a diode 342. The output of the diode 341 is connected to an input 343 of the flip-flop 221.

The limit switch 73 is connected, via a timer 344, to inputs 345, 346 and 347 of respective gates 348, 349 and 350. An input 351 of the gate 348 is connected to the output of the analog-to-digital converter 99. An input 352 of the gate 349 is connected to the output 90 of the counter 89. An input 353 of the gate 350 is connected to the output 84 of the counter 83. Outputs 354, 355 and 356 of the respective gates 348, 349 and 350 are connected to inputs 357, 358 and 359 of the generator 75.

An output 360 of the generator 75 is connected to the input 340 of the counter 244 and to the input of the diode 341.

The outputs of the digital-to-analog converters 93 and 96 are connected to inputs 361 and 362 of the visual display 76 whose input 363 is connected to the output 98 of the converter 49.

The limit switches 60 and 61 are connected to the input 322 of the flip-flop 325, the limit switches 68 and 69 are connected to the input 321 of the flip-flop 324, and the limit switches 65 and 66 are connected to the input 320 of the flip-flop 323. Inputs 364, 365 and 366 of the respective flip-flops 323, 324 and 325 are connected to an interlock release toggle switch 367.

Inputs 368, 369 and 370 of the gates 202, 297 and 206 are connected to outputs 371, 372, 373 of gates 374, 375 and 376, respectively. Inputs 377, 378 and 379 of the gates 374, 375 and 376 are connected to knob angle sensors 380, 381 and 382. Inputs 383, 384 and 385 of the gates 374, 375 and 376 are connected to an output 386 on a flip-flop 387.

The output 386 of the flip-flop 387 is connected, via an inverter 388, to inputs 389, 390 and 391 of the gates 201, 296 and 205. An output 392 of the gate 291 is connected to the input 368 of the gate 202 and an input 393 of the gate 201 is connected to the output of the control circuit 200. An output 394 of the gate 296 is connected to the input 369 of the gate 297, while an input 395 of the gate 296 is connected to the output of the control circuit 295. An output 396 of the gate 205 is connected to the input 370 of the gate 206, while an input 397 of the gate 205 is connected to the output of the control circuit 204.

An input 398 of the flip-flop 387 is connected to a push-button 399 of the function switch. An input 400 of the flip-flop 387 is connected to ON button 401 of the device. The button 401 and the output 386 of the flip-flop 387 are connected to inputs 402 and 403 of an OR gate 404 whose output 405 is connected, via a differentiating unit 406, to the input of the diode 341 and the input 340 of the pulse counter 244.

If one side of the trapezium 46 (FIG. 4) is formed as the parabola portion 47 and the diaphragm 4 is secured firmly in the barrel 2, the output of the differentiating unit 309 (FIG. 5a''') should be disconnected from the diaphragm drive 54 and tied up directly with the input of the timer 344 as shown by a dotted line 407.

Figure 5A:
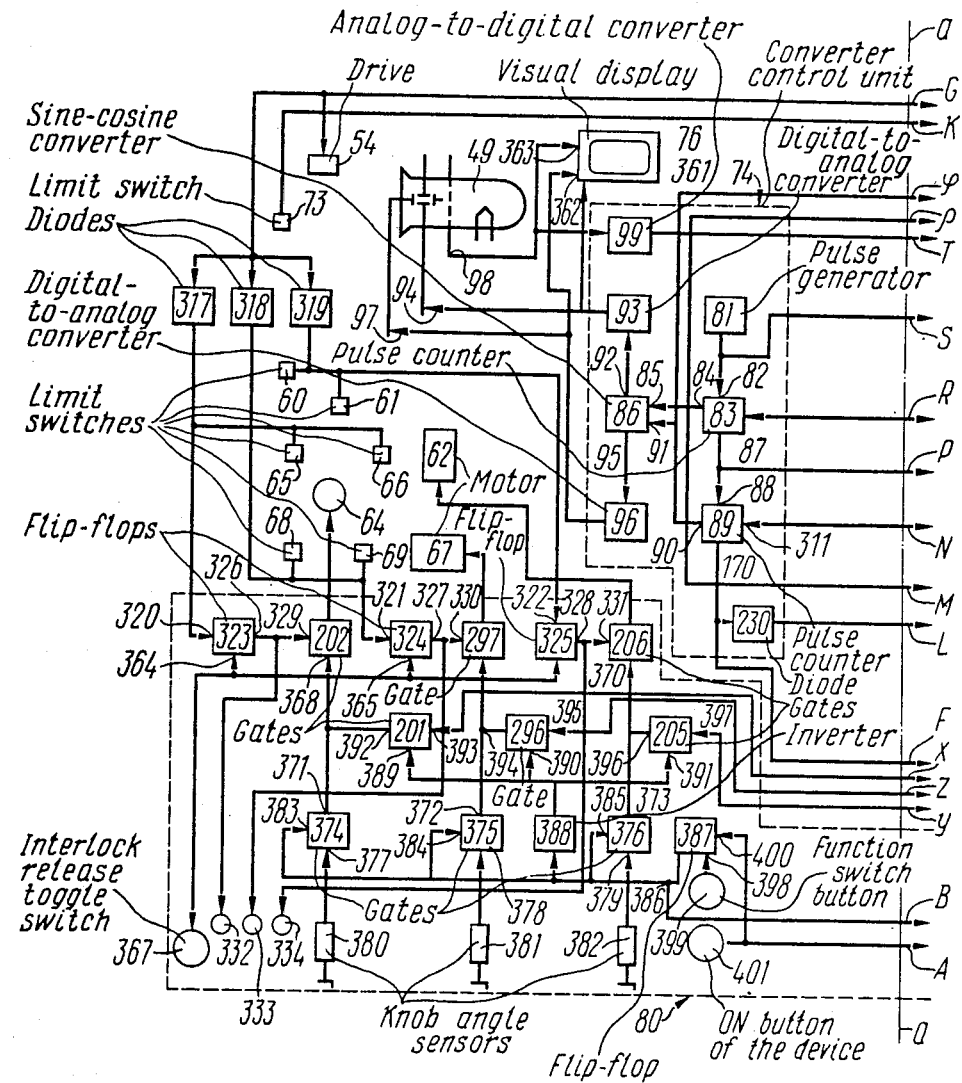
FIGS. 5a, 5a', 5a", and 5a''' show the functional diagram of a device for determining the cornea surface topography as embodied in FIG. 4, according to the invention.
Figure 5A:
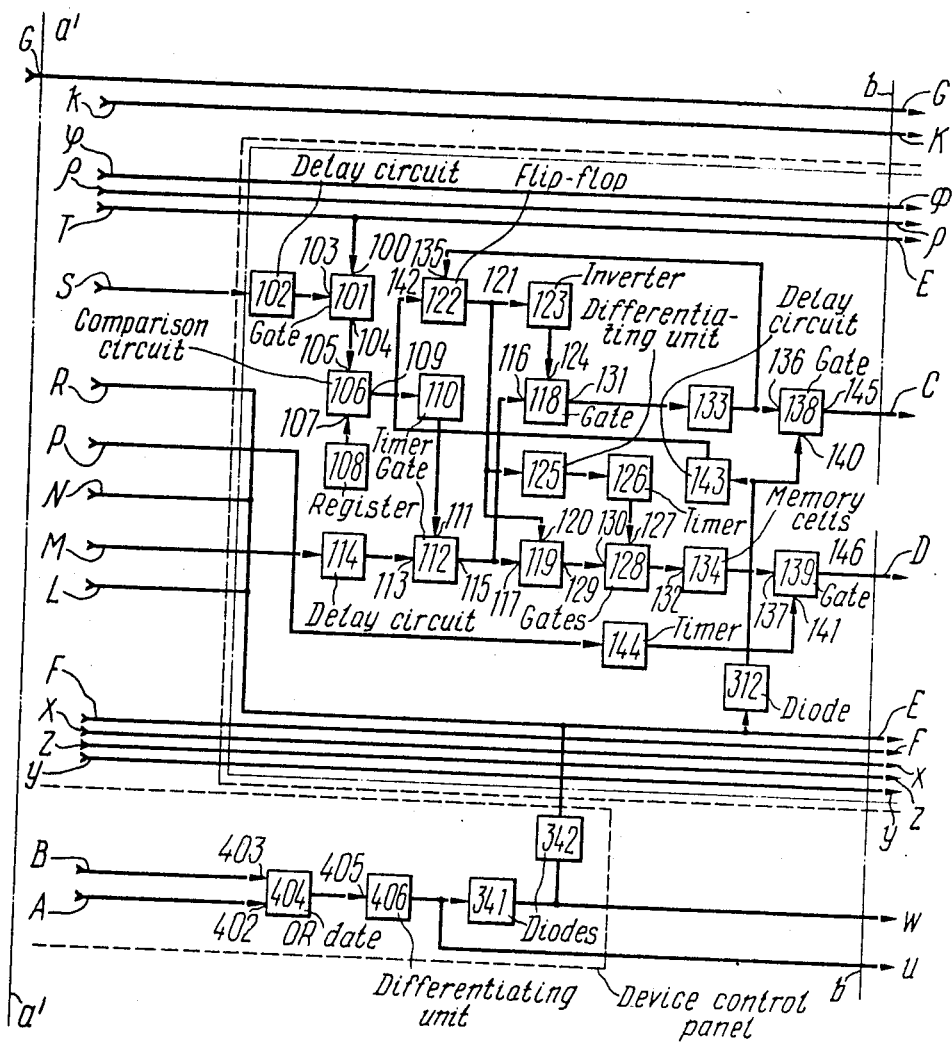
Figure 5A:
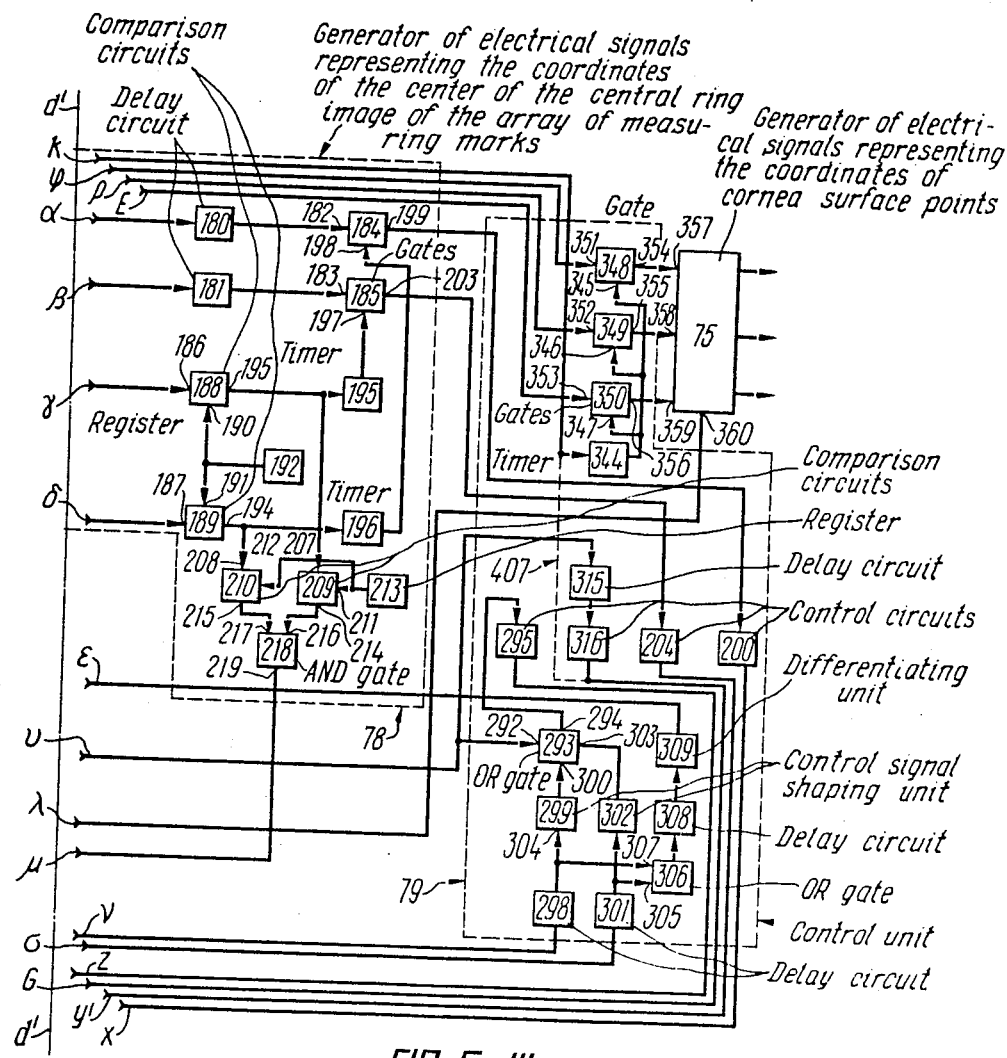

Letters at the side edges of FIGS. 5a, 5a', 5a'', and 5a''' indicate electrical connections between components in FIGS. 5a, 5a', 5a'', and 5a'''.

The sine-cosine converters 66 and 152 are built around circuits known for any person skilled on the art (cf., for example, F. Vaida, A Chakan'. Microcomputers. Energia Publ., Moscow, 1980, pp. 318, 319, in Russian).

The above mentioned computing units 149, 224, 290 are also built around known circuits (cf., for example, N. M. Nikitiuk. Microprocessors and Microcomputers. Their Use in Instrument Engineering and Scientific Research. Moscow, Energoizdat, 1981, pp. 131-133).

A device for determining the cornea surface topography operates as follows.

The patient is placed in front of the device for determining the cornea surface topography so that the eye to be examined is within the field of the lens 3 (FIG. 1). The operator moves the frame lengthwise, crosswise and vertically relative to the mounting 39 in order to obtain a sharp image of the central ring of the array of measuring marks in the eyepiece 18 of the camera 14 and to match the center of the line of the central ring image in the array of the measuring marks 9 with the center of the grid 19 lying on the optical axis of the eyepiece 18 which coincides with the axis 8 of the lens 3. These adjustments make the optical axis 8 of the lens 3 cut the cornea surface at 90° thereto and the focal plane $F_c$ is set at a fixed distance from the lens 3 and the measuring marks 9. It should be specified at this point that what the operator sees in the eyepiece 18 are not the images of the measuring marks 9 proper but the images of the annular luminous body 6 of the light source 5 formed by the reflective working surface 10 of the measuring marks 9.

The operator then has to obtain an approximately symmetrical image of the array of the measuring marks 9 and 9' in the field of the eyepiece 18 by making the patient change the direction of his focus. In consequence, the optical axis 8 of the lens 3 is matched with the axis or line of intersection of two symmetry planes of a symmetrical surface closest to the cornea surface. The results of determining the cornea surface topography are much simplier to decode in this case and they can be presented in a form convenient for assigning contact lenses.

While the above operations are performed, the diaphragm 4 is turned on the hinge 13 so as to avoid screening of the bundle of rays coming through the lens 3. In this case the depth of definition of the optical system is shallow. Lengthwise adjustment of the device becomes, therefore, more sensitive.

The adjustment being over, the diaphragm 4 is turned on the hinge 13 and set in the rear focal plane of the lens 3. The operator then presses the shutter release to actuate the camera 14 and record the image of the annular luminous body 6 of the light source on the film 20. Here the images of the luminous body 6 are formed by the reflective working surfaces 10 of the measuring marks 9 at distances approximately equal to the half radius of the meridian section of the working surface 10 and behind that surface. The reflecting surface of the cornea forms in turn a secondary image for the image produced by the working surface 10. This secondary surface is situated, approximately, in the focal plane of the reflecting cornea surface. The lens 3 projects said secondary image onto the film 20. Wide beam bundles passing the lens 3 are not let through by the diaphragm 4 which let pass only narrow bundles whose main beams go through the center of the opening of the diaphragm 4. Prior to the lens 3 they are arranged parallel to the optical axis 8 of said lens 3. The diaphragm 4 substantially increases the depth of definition of the optical system of the device. It becomes possible to obtain sharp images, on the film 20, of the annular luminous body 6 produced not only by the working surfaces 10 of the central measuring marks 9 and the central portion of the cornea but also of the peripheral measuring marks 9 and the peripheral portion of the cornea.

The analysis of images obtained is significantly simplified because the diaphragm 4 makes the main beams parallel to the optical axis of the lens 3. This analysis can use the technique described in Le Contact magazine No. 25, 1967, p. 7.

The screen 12 shields the direct light of the light source 5 from getting into the cornea.

The film 20 which recorded the images of the annular luminous body 6 of the light source 5 is processed, measured and analyzed in accordance, for example, with the above technique. The analysis is done by comparison of the obtained picture with a standard image on the assumption that the angles between the main beam bundles producing the images of the luminous body 6 and the optical axis of the lens 3, when incident upon the cornea surface and the standard surface, are equal and constant for any cornea surfaces. In case of the device of FIG. 1 this assumption is definitely wrong, the ensuing errors being particularly drastic for cornea surfaces whose asphericity, which may be defined as irregularity of the curvature radius from the center towards the periphery, is substantial. To minimize these errors the distances from the cornea surface to the secondary images of the luminous body 6 formed by the reflective working surfaces 10 should be lengthened. When the cross-section of the annular marks 9 is shaped like the circle 11, the above objective can only be attained by making the entire device larger.

The device of FIG. 2 operates completely analogous to that of the FIG. 1. The only difference is that the working surface 10 of the measuring marks 9 shaped in their cross-section like the trapezium 46 forms a secondary image of the luminous body 6 behind the working surface 10 at a distance equal to the separation between the axis 48 of the luminous body 6 and the working surface 10. This permits either higher accuracy of determining the cornea surface topography within the same dimensions of the device or, on the contrary, reduction of the device size with the same accuracy of measurements.

The device of FIG. 3 is basically similar to that of FIG. 1 in operation. The difference consists in that, when the cross-section of the measuring marks 9 is formed as the trapezium 46 whose side is the parabola portion 47, the working surface 10 of said measuring marks 9 produces a secondary image of the axis 48 of the luminous body 6 at an infinitely large distance relative to the working surface 10 and the cornea surface. The working surfaces 10 form parallel bundles of beams inclined to the optical axis 8 at different angles. Here the assumption about the beam incidence angles being constant for any cornea surfaces holds true and the accuracy of determining the cornea surface topography is appreciably improved.

The operation of the device of FIG. 3 can be somewhat simplified as compared to the embodiment of FIG. 1. The diaphragm 4 may be set stationary in the focal plane of the lens 3. Lower sensitivity of lengthwise adjustment will have no effect on the accuracy of determining the cornea surface topography because in this embodiment, unlike in previous ones, an error in the lengthwise adjustment of the measuring marks 9 with respect to the focal plane of the central portion of the cornea reflective surface will not change the angles of incidence of the main bundles of beams passing from the working surface 10 onto the cornea surface relative to the optical axis 8.

As the angles of incidence of said beams are constant, errors in crosswise adjustment, that is the matching of the optical axis 8 with the perpendicular to the cornea surface, have a considerably weaker effect upon the results of determining of the cornea surface topography.

The electronic circuit of the device of FIG. 4 operates as follows.

The device is switched on by the pushbutton 401 (FIG. 5a) on the control panel 80 and all components of the electrical circuit are energized. The pushbutton 401 sends a pulse to the input 400 of the flip-flop 387 to reset it. The flip-flop 387 is put into the "0" state and the signal at the output 386 thereof keeps the gates 374, 375 and 376 opened via the inputs 383, 384 and 385. The signal from the output 386 of the flip-flop 387 is applied, via the inverter 388, to the inputs 389, 390 and 391 of the gates 201, 296 and 205 keeping them closed.

As soon as the device is switched on, the signal from the pushbutton 401 is supplied, via the OR gate 404 and the differentiating unit 406, to the input 340 of the counter 244 to reset it and, via the diode 341, to the input 343 of the flip-flop 221 to set it to zero. In addition, the signal from the pushbutton 401 is supplied, via the OR gate 404, the differentiating unit 406 and diodes 341 and 342, to the inputs 310 and 311 of the counters 83 and 89 to reset them and, via the delay circuit 229, to the adder 227 to reset it. A signal from the pushbutton 401 is also delivered, via the OR gate 404, the differentiating unit 406, the diodes 341, 342 and 312 and the delay circuit 143, to the input 142 of the flip-flop 122 to reset it. A signal from the output of the diode 342 is applied, via the diodes 313 and the delay circuit 314, to the inputs 178 and 179 to reset the adders 159 and 160.

The device being switched on, the interlock is released by means of the toggle switch 367 which resets the flip-flops 323, 324 and 325 by applying signals to their inputs 364, 365 and 366. Output signals of these flip-flops open the gates 202, 297 and 206.

The generator 81 produces pulses to be supplied to the input 82 of the counter 83 to increase the content thereof. A signal taken from the output 84 of the counter 83, which is proportional to its content, is transmitted to the input 85 of the computing unit 86. When the counter 83 overflows, a signal from the output 87 is applied to the input 88 of the counter 89 and increases the content thereof. A signal from the output 90 of the counter 89 is supplied to the input 91 of the computing unit 86. Signals of the counters 83 and 89 represent the radial coordinate $\rho$ (FIG. 6) and the angular coordinate $\phi$ of the scanning point of the converter 49 (FIG. 5a). The computing unit 86 converts the signals proportional to the radial and angular coordinates of the scanning point into signals proportional to the rectangular coordinates x and y thereof. These signals are taken from the outputs 92 and 95 of the computing unit 86, via the digital-to-analog converters 93 and 96, to the control inputs 94 and 97 of the converter 49 and to the inputs 361 and 362 of the visual display 76.

The signal from the output 98 of the converter 49, which is proportional to the illumination intensity of the image in the scanning point, is applied to the input 363 of the visual display 76.

The patient is placed in front of the device so that his eye is in the field of the lens 3 (FIG. 4). The operator watches the picture on the screen of the visual display 76 and controls the operation of the motors 64, 67 and 62 by turning knobs of the angle sensors 380, 381 and 382, the gates 374, 375, 376 and 202, 297, 206 being opened.

The motor 62 (FIG. 4) moves, by means of the worm gearwheel 63 and the helix rack 58, the frame 1 having a vertical guide 25 along the vertical guide 22.

The motor 67 moves the platform 30 having the threaded opening 72 relative to the mounting 39 by means of the shaft 70 having the thread 71.

Similarly, the motor 64 moves the platform 21 relative to the platform 30.

In this manner the frame 1 is moved vertically (along the y axis), crosswise (along the x axis) and lengthwise (along the z axis) relative to the cornea surface.

The frame 1 is thus adjusted until the image produced by an array of the measuring marks 9 via the converter 49 on the screen of the visual display is sharp enough and the center of the central ring of the array of the measuring marks 9 is approximately in the center of the screen.

The patient is then told to change the direction of his sight until the operator obtains an approximately symmetrical arrangement of the measuring marks 9 on the screen.

If the movements of the frame 1 make one of the limit switches 60, 61, 65, 66, 68, 69 operate indicating that the frame 1 reached the limit in vertical, longitudinal or lateral directions, one or several flip-flops 323, 324 or 325 are set to "1", thus lighting up the indication lamps 332, 333, 334 and closing the gates 202, 297 and 206 denying the control signals access to the motors 64, 67 and 62.

To release the interlock of the device, the operator should press the toggle switch 367 and, keeping it pressed, turn the knobs of the sensors 380, 381 and 382 to actuate the motors 64, 67 and 62 to move the frame 1 to some middle position. The toggle switch 367 is then reset. The patient is placed in front of the device so that his cornea is closer to an optimal position than it was when the device had come to interlock.

Following the preliminary adjustments the operator sets the device for automatic operation. For this the operator presses the button 399 which sets the flip-flop 387 to "1" state. The signal from the output 386 of the flip-flop 387 is supplied to the inputs 383, 384 and 385 of the gates 374, 375 and 376 to close them and to open, via the inverter 388, the gates 201, 296 and 205 letting pass control signals from the control unit 79 to the motors 64, 67 and 62. When the flip-flop 387 is set, the output of the differentiating unit 406 sends a signal which resets the counter 244, the counters 83 and 89, the adders 150, 160, 227 and the flip-flop 221.

Figure 7:
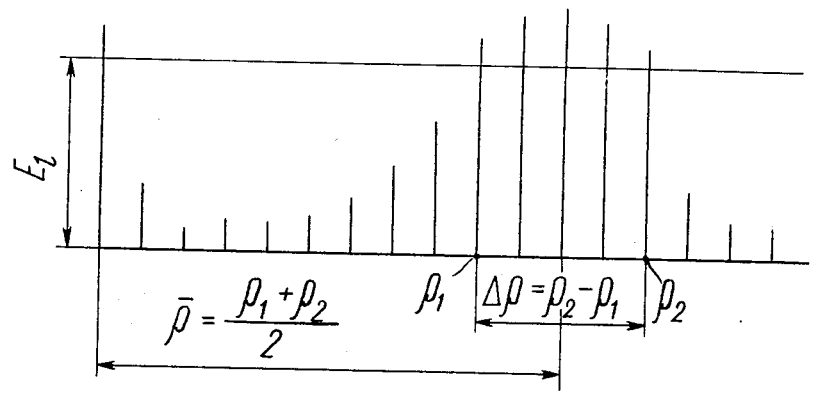
FIG. 7 shows electrical output signals of a converter of an optical image into electrical signals, according to the invention.

The signal representing the illumination intensity in the scanning point is transmitted from the output 98 of the converter 49, via the analog-to-digital converter 99, to the input 100 of the gate 101 which is by this moment is opened by the pulse delivered by the generator 81 through the delay circuit 102. This signal proportional to the illumination intensity in the scanning point is fed, via the gate 101, to the comparison circuit 106 wherein said signal is compared with the signal supplied from the register 108. This signal supplied from the register 108 sets a specific level of comparison. If the signal proportional to the illumination intensity is less than the signal from the register 108, the comparison circuit 106 produces no signal to actuate the timer 110 and keeps the gate 112 closed. If the signal proportional to the illumination intensity exceeds the level of the signal $E_1$ (FIG. 7), the comparison circuit 106 (FIG. 5a) produces a signal to actuate the timer 110. The signal of the timer 110 keeps the gate 112 open for the period needed to let pass the signal proportional to the radial coordinate of the scanning point from the output 84 of the counter 83 via the delay circuit 114 to the inputs 116 and 117 of the gates 118 and 119. When the gate 112 opens for the first time, the flip-flop 122 is reset and the signal from the output 121 thereof closes the gate 119 and opens, via the inverter 123, the gate 118. In consequence, the signal proportional to the radial coordinate $\rho$ of the scanning point where the signal proportional to the illumination intensity exceeded, for the first time, the threshold level $E_1$ (FIG. 7) is sent to the memory cell 133 (FIG. 5a') and stored therein. The signal from the output of the memory cell 133 is delivered to the input 135 of the flip-flop 122 and sets it, thus closing the gate 118 and opening the gate 119.

The signal passing from the output 121 of the flip-flop 122 via the differentiating unit 125 activates the timer 126 which keeps the gate 128 open. All subsequent radial coordinates of scanning points will be recorded in the memory cell 134 through this gate 128 until the signal proportional to the illumination intensity becomes again less than the level $E_1$, which corresponds to the outermost boundary of the central ring of the image. In this manner the memory cell 134 will store the radial coordinate $\rho_o$ (FIG. 7) representing the external boundary of the image central ring, while the memory cell 133 (FIG. 5a') will store the coordinate $\rho_1$ (FIG. 7) representing the inner boundary thereof.

After the radial coordinate of the external boundary of the image central ring is stored in the memory cell 134 (FIG. 5a), the timer 126 completes its operation and closes the gate 128. The contents of the memory cells 133 and 134 are not, therefore, altered when the scanning point crosses the images of subsequent rings.

Figure 6:
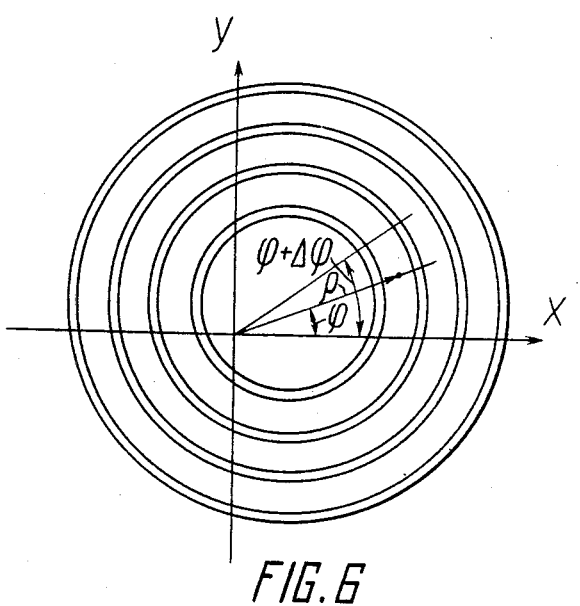
FIG. 6 shows an image of an array of measuring marks on the sensitive element of a light detector, according to the invention.

The one scanning line being completed, the counter 83 produces a signal at the output 87 thereof, which increases the contents of the counter 89. Thus starts scanning at some new angle $\alpha + \Delta\phi$ (FIG. 6). The signal outgoing from the output 87 of the counter 83 is fed to the timer 144 and actuates it. While the timer 144 is engaged, the gates 138 and 139 are opened and let pass signals from the memory cells 133 and 134 to the computing units 149 and 224. After that the signal of the timer 144 resets the flip-flop 122 via the delay circuit 143, thus setting the electronic circuit of the device into the initial position ready for scanning at the new angle $\phi + \Delta\phi$ (FIG. 6).

The computing unit 149 (FIG. 5a'') develops a signal at the output 150, which is proportional to $\bar{\rho}$ equal to $$\bar{\rho} = \frac{\rho_1 + \rho_2}{2}$$

and representing the radial coordinate of the middle of the image line of the central ring. This value is applied to the input 151 of the sine-cosine converter 152 whose other input 153 accepts a signal representing the angular coordinate $\phi$ of the middle of the image line of the central ring coming from the output 90 of the counter 89 via the subtraction circuit 154 which deducts the increment $\Delta\phi$ from the current signal proportional to $\phi + \Delta\phi$. The sine-cosine converter 152 generates, at the outputs 155 and 156 thereof, signals proportional to the crosswire coordinate x and the vertical coordinate y of the middle of the image line of the central ring in the meridian corresponding to the angle $\phi$. These coordinates are added to the contents of the adders 159 and 160.

Scanning at other angles $\phi$ yields lateral and vertical coordinates x and y of the middles of the image line of the central ring in different meridians. The adders 159 and 160 sum these coordinates up. When the angle $\phi$ reaches 360°, the counter 89 works out, at the output 170 thereof, a signal to open the gates 165 and 166. These gates 165 and 166 let pass the contents of the adders 159 and 160, which corresponds to the vertical and lateral coordinates of the center of the image of the central ring, to the inputs 187 and 186 of the comparison circuits 189 and 188 wherein this contents is compared with the contents of the register 192, which corresponds to the maximum rated deviation of the image center of the central ring from the scanning center coinciding with the optical axis 8 (FIG. 4) of the lens 3. If the coordinates of the image center exceed the limits of permissible deviation, a respective comparison circuit 189 or 188 (FIG. 5a''') opens, via the timers 196 and 195, the gates 184 and 185 letting through the contents of the adders 159 and 160 to the control circuits 200 and 204 of the control unit 79 developing signals controlling the motors 64 and 62, whose magnitude and sign corresponds to respective lateral coordinate x and vertical coordinate y of the image center. The frame 1 (FIG. 4) moves and the image center approaches the scanning center, which is an automatic process of matching the perpendicular to the cornea surface with the optical axis 8 meant to eliminate subjective operator's errors.

After passing through the gates 165 and 166 (FIG. 5a'') the signals are supplied, via the OR gate, to the differentiating unit 177 working out a pulse in order to reset the adders 159 and 160.

In case the coordinates of the image center of the central ring are within the allowance, the comparison circuits 188 and 189 produces no signals. Zero signals appear, therefore, at the inputs 207 and 208 of the comparison circuits 209,210. By comparing these zero signals with the contents of the register 213 equal to zero the comparison circuits 209 and 210 work out signals permitting the beginning of lengthwise adjustment. These signals are fed to the AND gate 218 which can generate a signal only when both inputs 216 and 217 accept non-zero signals, that is when the vertical and lateral coordinates y and x of the image center are within the permissible limits. The signal generated by the AND gate 218 sets the flip-flop 221 which opens the gate 239 actuating the generator 77 of signals representing the mean linewidth of the central ring image.

Signals from the outputs 145 and 146 of the gates 138 and 139 are conveyed to the inputs 223 and 222 of the computing unit 224 which calculates the width $\Delta\rho$ (FIG. 7) of the line of the central ring image in a meridian arranged at some angle $\phi$:

$$\Delta\rho = \rho_2 - \rho_1. \tag{1}$$

A signal proportional to the linewidth $\Delta\rho$ is transmitted from the output 225 (FIG. 5a'') of the computing unit 224 to the input 226 of the adder 227 wherein it is summed up with the contents thereof.

After completing the full scanning cycle from 0° to 360°, a signal is produced at the output 170 of the counter 89 and increases the contents of the counter 244 by one. At first, consequently, the contents of the counter 244 becomes "one" to be conveyed to the comparison circuits 249, 250 and 251 wherein it is compared with the quantities 1, 2 and 3 set in the registers 255–257. Here, the contents of the counter 244 is still equal to the contents of the register 255. Then the comparison circuit 249 actuates the timer 259 which opens the gate 235 to let pass the contents of the adder 227, which is, at this stage, proportional to the mean linewidth $\Delta\rho_o$ of the central ring image, to the memory cell 270. The longitudinal coordinate Z of the device relative to the cornea surface is, at this moment, assumed to be "0". Concurrently with the opening of the gate 235, the comparison circuit 249 initiates, via the delay circuit 298, the actuation of the generator 299 which produces a signal and furnishes it, via the OR gate 293, to the control circuit 295 to move the frame 1 to a distance Z. The comparison circuit 249 gives out a signal, via the delay circuit 298, the OR gate 306 and the delay circuit 308, to the differentiating unit 309 whose pulse resets the counters 83 and 89, the adders 159, 160 and 227, and the flip-flop 122.

A second scanning cycle is started thereafter. At the end of this second scanning cycle the counter 89 increases the contents of the counter 244, the comparison circuit 250 operates because the contents of the register 256 coupled thereto becomes, at this moment, equal to the contents of the counter 244. The comparison circuit 250 actuates the timer 262 which opens the gate 236 to let pass the contents of the adder 227 equal to the mean linewidth $\Delta \rho_1$ of the image, the longitudinal coordinate of the frame relative to the cornea surface being $Z_1$, to the memory cell 271. Then the output signal of the comparison circuit 250 actuates, via the delay circuit 301, the generator 302 which supplies a signal, via the OR gate 293, to the control circuit 295 to move the frame into a position whose longitudinal coordinate is $Z_2$. At the end of the scanning cycle the comparison circuit 250, similar to the comparison circuit 249, resets the counters 83, 89, the adders 159, 160, 227 and the flip-flop 122.

When the next, third, scanning cycle is completed, the contents of the counter 244 becomes equal to the contents of the register 257. The comparison circuit 251 opens, via the timer 265, the gate 237 which lets pass the contents of the adder 227 equal, at that moment, to the mean linewidth $\Delta \rho_2$ of the image, the longitudinal coordinate of the frame relative, to the cornea surface being $Z_2$, to the memory cell 272. Then the comparison circuit 251 opens, via the delay circuit 283 and the timer 282, the gates 276, 277 and 278 which let pass the contents of the memory cells 270, 271 and 272 to the inputs 287, 288 and 289 of the computing unit 290.

The computing unit 290 determines a coordinate $Z_{min}$ representing the minimal linewidth of the central ring image. To this end, the computing unit 290 determines coefficients a, b and c of the parabola extending through the points having the following coordinates: /0, $\Delta \rho_0$/, /$Z_1$, $\Delta \rho_2$/ and /$Z_2$, $\Delta \rho_2$/. Then a signal is transmitted from the output 291 of the computing unit 290 via the OR gate 293 to the control circuit 295, this signal being proportional to the coordinate $Z_{min}$. The frame is moved into a position corresponding to the coordinate $Z_{min}$ by a signal from the output of the control circuit 295.

A signal from the output 291 of the computing unit 290 is transmitted, via the delay circuit 315, to the control circuit 316 which works out a signal to actuate the drive 54 of the diaphragm 4 (FIG. 4). The diaphragm is set in the barrel 2 and actuates the limit switch 73 (FIG. 5a) which produces a signal to cut off the timer 344 thus opening the gates 348, 349 and 350 and let the generator 75 receive signals proportional to the radial and angular coordinates of the scanning point and the illumination intensity therein during a full scanning cycle. The generator 75 processes these signals in accordance with a specific program, such as claimed, for example, in the FRG Pat. No. 2,641,004. The generator 75 produces digital or analog signals representing the coordinates of the cornea surface points.

The present embodiment of the invention is also equipped with components to take care of errors caused by patient's blinking during measurements. If the patient blinks in the process of adjustment, the coordinates $\rho_1$ and $\rho_2$ of the inner and outer boundaries of the central ring are equal to zero after scanning at an angle $\phi$. The signals at the outputs 150 and 225 of the computing units 149 and 224, which are conveyed to the inputs 335 and 337 of the comparison circuit 336, are also equal to zero. When signals at the inputs 335 and 337 of the comparison circuit 336 are equal, the output 338 gives out a signal which resets, via the differentiating unit 339, all counters, registers and flip-flops of the devices into their initial state and the adjustment of the device starts anew.

If the measuring marks 9 in the device of FIG. 4 have a cross-section shaped like the trapezium 46 whose one side is the parabola portion 47 and the diaphragm 4 is firmly secured in the barrel 2, the output signal of the differentiating unit 316 (FIG. 5a''') is directly applied to the input of the timer 344 which makes open the gates 348-350.

A method for determining the cornea surface topography, realized by all above embodiments of a device, is described, for simplicity, for the embodiment of FIG. 1 only.

If the normal to the cornea surface in the point of reflection of the beam lies out of the meridian plane, the beam incident upon the cornea is also out of said meridian plane.

This beam originates not in the point N (FIG. 8) of the measuring mark 9 but in the point M located at some angle $\epsilon_K$ (FIG. 9) relative to the point N. If the deviation of the incident beam from the meridian plane is disregarded, the angle $2\alpha_K$ (FIG. 8) of projection of the incident beam onto the meridian plane relative to the optical axis 8 (FIG. 1) of the lens 3 can be determined with an error $\Delta \alpha_K$ relative to the specified topographic angle. The magnitude of the error $\Delta \alpha_K$ depends on the angle $\gamma_K$ (FIG. 10) of deviation of the normal to the cornea surface from the meridian plane. This deviation can be quite large for corneas of complex and irregular shapes.

In order to correct this error the angle $\gamma_K$ of inclination of the normal to the cornea surface in the sagittal plane should be determined by means of the measuring marks 9'-the radial grid. The angle $\gamma_K$ on the image of the measuring marks 9 and 9' in the plane of the film 20 (FIG. 10) is determined by measuring the angle $\epsilon_K$ (FIG. 11) between the images of the same intersection points of the measuring marks 9,9' on the cornea surface and on the standard axially-symmetric surface. The angle $\gamma_K$ is determined according to the formula:

$$\gamma_K = \epsilon_K/2 \qquad (2)$$

Then an allowance is introduced into the specified topographic angles $\alpha_K$, varying with the angle $\gamma_K$, in accordance with the formula:

$$\alpha_K = \text{arc tg} \frac{R_K \cos(2\gamma_K)}{a_k}, \qquad (3)$$

where
  $R_k$ is the radius of the k-th ring of the measuring mark;

$a_k$ is the distance from the k-th ring of the measuring mark to the focus of the cornea reflective surface.

What is claimed is:

1. A method for determining cornea surface topography, comprising the steps of:

projecting an array of intersecting measuring marks onto the cornea, said array being formed by a plurality of annular marks producing, when projected onto the cornea, several concentric ring-shaped patterns and by a plurality of linear marks intersecting the annular marks substantially at right angles and forming, when projected onto the cornea, a circular grid including radii;

obtaining a flat image of the array of measuring marks projected onto the cornea;

measuring the radial coordinates of points defined by the intersection of linear and annular marks on said flat image for specified topographic angles;

measuring the angular coordinates of said points relative to corresponding points of intersection of linear and annular marks on a flat axially symmetric image of said array of measuring marks;

correcting said specified topographic angles in accordance with said measured coordinates of said points on the grid.

2. A device for determining cornea surface topography, comprising:

a mounting;

a curved frame having a concave surface and an axis and movable relative to said mounting;

projection means including a light source secured on said frame adjacent said concave surface;

a lens installed in said frame between said light source and said light detector;

an array of measuring marks carried on the concave surface of said frame;

said measuring mark array comprising a combination of two groups of marks, one said group being a plurality of annular marks arranged one after another in spaced relationship axially along the axis of the concave surface of said frame in planes perpendicular to said axis, while the other said group is a plurality of lines arranged in respective planes passing through and parallel to said axis and extending lengthwise along the concave surface of said frame, said projection means adapted to project said measuring mark array onto a cornea positioned on said axis of said concave surface;

detecting means including a light detector secured on said frame and having a flat surface for detecting reflections from a cornea of each of said lines intersecting each of said annular marks and producing on said surface of said light detector a flat image of concentric ring-shaped patterns and radial grid lines intersecting said patterns as reflected by a cornea to permit a determination of the topography of the surface of the cornea.

3. A device as claimed in claim 2, wherein said annular marks are reflective.

4. A device as claimed in claim 3, wherein said annular marks have a cross-section shaped like a circle.

5. A device as claimed in claim 4, comprising:

a converter included in said light detector for converting an optical image into an electrical signal, and having a group of outputs;

means for providing electrical signals representing the coordinates of cornea surface points, which means has a group of inputs and outputs, said inputs being electrically connected to respective outputs of said converter;

a visual display having a group of inputs, said inputs being electrically connected to respective outputs of said converter.

6. A device as claimed in claim 5, comprising:

means for providing electrical signals representing the mean linewidth of the central ring image of said array of measuring marks and having a group of inputs and outputs, said inputs being electrically connected to respective outputs of said converter;

means for providing electrical signals representing the coordinates of the central ring image center of said array of measuring marks and having a group of inputs and outputs, said inputs being electrically connected to respective outputs of said converter;

drive means secured to said frame in order to move said frame relative to said mounting;

control means having a group of inputs and outputs, said inputs being electrically connected to said outputs of said means for providing electrical signals representing the mean linewidth of the central ring image of said array of measuring marks and said means for providing electrical signals representing the coordinates of the central ring image center, and said outputs being electrically connected to said drive means to control said drive means, according to which said frame moves relative to said mounting in longitudinal, lateral and vertical directions in order to match the optical axis of said lens with the axis of the cornea being examined and to set the device at a specified distance from the focal plane of the reflecting surface of said cornea.

7. A device for determining cornea surface topography, comprising:

a mounting;

a curved frame having a concave surface and an axis and movable relative to said mounting;

projection means including a light source secured on said frame adjacent said concave surface and including an annular luminous body having an axis coincident with the axis of said concave surface;

a lens installed in said frame and positioned in an optical path between said light source and said light detector;

a diaphragm carried in said frame between said lens and said light detector;

an array of measuring marks carried on the concave surface of said frame;

said array of measuring marks comprising a combination of two groups of marks, one said group being a plurality of annular marks arranged one after another in spaced relationship axially along the axis of the concave surface of said frame in planes perpendicular to the optical axis of said lens, while the other said group is a plurality of lines arranged in respective planes passing through and parallel to said axis and lengthwise along the concave surface of said frame, said projection means adapted to project said measuring mark array onto a cornea positioned on said axis of said concave surface;

detecting means including a light detector secured in said frame and having a flat surface for detecting reflections from a cornea of each of said lines intersecting each of said annular marks, thus producing on said surface of said light detector a flat image of concentric ring-shaped patterns and radial grid lines intersecting said patterns as reflected by a cornea to permit a determination of the topography of the surface of the cornea.

8. A device as claimed in claim 7, wherein said annular marks are made reflective and the cross-section thereof is shaped like a trapezium.

9. A device as claimed in claim 8, wherein one side of said trapezium, facing the optical axis of said lens is a portion of a parabola arranged so that the focal point thereof coincides with the axis of said luminous body.

10. A device as claimed in claim 9, comprising:
a converter included in said light detector for converting an optical image into an electrical signal, and having a group of inputs;
means for providing electrical signals representing the coordinates of cornea surface points and having a group of inputs and outputs, said inputs being electrically connected to respective outputs of said converter;
a visual display having a group of inputs electrically connected to respective outputs of said converter.

11. A device as claimed in claim 10, comprising:
means for providing electrical signals representing the mean linewidth of the central ring image of said array of measuring marks and having a group of inputs and outputs, said inputs being electrically connected with respective outputs of said converter;
means for providing electrical signals representing the coordinates of the center of the central ring image of said array of measuring marks and having a group of inputs and outputs, said inputs being electrically connected with respective outputs of said converter;
drive means secured to said frame in order to move said frame relative to said mounting;
control means having a group of inputs and outputs, said inputs being electrically connected with said outputs of said means for providing electrical signals representing the mean line width of the central ring image and said means for providing electrical signals representing the coordinates of the center of the central ring image, said outputs being electrically connected with said drive means to control said drive means, according to which said frame moves, relative to said mounting, in longitudinal, lateral and vertical directions in order to match the optical axis of said lens with the axis of the cornea and to set the device at a specified distance from the focal plane of the reflective surface of said cornea.

* * * * *